(12) United States Patent
Christakis et al.

(10) Patent No.: US 10,070,862 B2
(45) Date of Patent: Sep. 11, 2018

(54) ENDOSCOPIC STAPLES INCLUDING ANCHORAGE MECHANISMS

(71) Applicant: Boston Scientific Scimed, Inc., Maple Grove, MN (US)

(72) Inventors: Laura E. Christakis, Worcester, MA (US); Sean P. Fleury, Brighton, MA (US); Liam K. P. M. Rolle, Boston, MA (US); Colby Harris, Weston, MA (US); Paul Smith, Smithfield, RI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 358 days.

(21) Appl. No.: 14/840,696

(22) Filed: Aug. 31, 2015

(65) Prior Publication Data

US 2016/0066908 A1    Mar. 10, 2016

Related U.S. Application Data

(60) Provisional application No. 62/048,437, filed on Sep. 10, 2014.

(51) Int. Cl.
*A61B 17/068* (2006.01)
*A61B 17/064* (2006.01)
*A61B 17/00* (2006.01)

(52) U.S. Cl.
CPC .......... *A61B 17/068* (2013.01); *A61B 17/064* (2013.01); *A61B 2017/00557* (2013.01); *A61B 2017/0649* (2013.01)

(58) Field of Classification Search
CPC .............. A61B 17/064; A61B 17/0645; A61B 2017/0435; A61B 2017/0437; A61B 17/068
See application file for complete search history.

(56) References Cited

U.S. PATENT DOCUMENTS

2005/0283189 A1* 12/2005 Rosenblatt ......... A61B 17/0401
606/216

* cited by examiner

*Primary Examiner* — Thomas McEvoy
(74) *Attorney, Agent, or Firm* — Fay Kaplun & Marcin, LLP (57) ABSTRACT

A device for closing a tissue opening includes a body extending from a first end to a second end and a first anchoring element connected to the first end of the body and a second anchoring element connected to the second end of the body. At least one of the first anchoring element and the second anchoring element is movable between an insertion configuration, in which the at least one of the first and second anchoring elements is insertable through a target tissue such that the body extends across a tissue opening to be treated, and an anchoring configuration, in which the first and second anchoring elements engage target tissue on a first side and a second side, respectively, of the tissue opening.

4 Claims, 7 Drawing Sheets

ENDOSCOPIC STAPLES INCLUDING ANCHORAGE MECHANISMS

PRIORITY CLAIM

The present disclosure claims priority to U.S. Provisional Patent Application Ser. No. 62/048,437 filed Sep. 10, 2014; the disclosure of which is incorporated herewith by reference.

BACKGROUND

Physicians have been increasingly willing to perform more aggressive interventional and therapeutic endoscopic procedures including, for example, the removal of larger lesions (e.g., cancerous masses), tunneling under the mucosal layer of the gastrointestinal (GI) tract to treat tissue below the mucosa, full thickness removal of tissue, the treatment of issues on other organs by penetrating and passing of the GI tract, and the endoscopic treatment/repair of post-surgical issues (e.g., post-surgical leaks, breakdown of surgical staple lines, anastomic leaks). These procedures my increase the risk of perforating the wall of the GI tract, or may require closure of the GI tract wall as part of the procedure. Endoscopic stapling devices may be used to treat such tissue openings/perforations. Current stapling devices, however, may prove difficult to use and/or may be insufficient to close certain perforations or to treat certain conditions.

SUMMARY

The present disclosure is directed to a device for closing a tissue opening, comprising a body extending from a first end to a second end along with a first anchoring element connected to the first end of the body and a second anchoring element connected to the second end of the body, at least one of the first anchoring element and the second anchoring element movable between an insertion configuration, in which the at least one of the first and second anchoring elements is insertable through a target tissue such that the body extends across a tissue opening to be treated, and an anchoring configuration, in which the first and second anchoring elements engage target tissue on a first side and a second side, respectively, of the tissue opening.

In an embodiment, the body may further include a first leg extending laterally from the first end of the body with the first anchoring element extending along a portion thereof and a second leg extending laterally from the second end with the second anchoring element extending along a portion thereof.

In an embodiment, the first leg and the second leg may extend substantially perpendicular to the body and parallel to one another.

In an embodiment, the body extends along a curve.

In an embodiment, the body is biased to extend along the curve.

In an embodiment, at least one of the first and second anchoring elements may include a first portion and a second portion pivotally coupled to one another at a pivot point, the first and second portions pivoting between the anchoring configuration, in which the pivot point extends away from a corresponding one of the first and second ends, and the insertion configuration, in which the pivot point moved toward the first and second legs.

In an embodiment, each of the first and second anchoring elements may be formed from a cut portion of the body that is cut away from an exterior surface thereof, the cut portion extending from a first end connected to the body to a second free end, the second end of the cut portion biased away from a remaining portion of the body in the anchoring configuration, and movable toward the remaining portion of the body in the insertion configuration.

In an embodiment, at least one of the first and second anchoring elements may be an inflatable bulb, the inflatable bulb being inflated in the anchoring configuration and deflated in the insertion configuration.

In an embodiment, at least one of the first and second anchoring elements may be a cap couplable to a corresponding one of the first and second ends of the body.

The present disclosure is also directed to a device for closing a tissue opening, comprising an outer member biased to extend along a curve from a distal end to a proximal end and including a first lumen extending therethrough in combination with an inner member slidably received within the first lumen of the outer member and movable relative thereto between an insertion configuration and an anchoring configuration, the inner member being biased to extend along a curve from a distal end to a proximal end, wherein, in the insertion configuration, the distal end of the inner member is received within a proximal portion of the first lumen, and, in the anchoring configuration, the inner member is moved distally relative to the outer member such that the distal end thereof extends distally past the distal end of the outer member and a first anchoring element connected to the proximal end of the inner member such that, in the anchoring configuration, the first anchoring element extends proximally from the proximal end of the outer member to anchor the device in a target tissue.

In an embodiment, the inner member may include a second lumen extending therethrough.

In an embodiment, the device may further comprise a second anchoring element connected to the distal end of the outer member.

In an embodiment, each of the first and second anchoring elements may be an inflatable bulb, the inflatable bulb deflated in the insertion configuration and inflated in the anchoring configuration, the first lumen of the outer member including an inflating fluid therein so that, when the inner member is moved distally relative to the outer member from the insertion configuration to the anchoring configuration, the inflating fluid is displaced, filling the inflatable bulb of the first and second anchoring elements.

In an embodiment, the inner member may be a wire including a second anchoring element at the distal end thereof, each of the first and second anchoring elements being formed via a portion of the wire biased to bend laterally away from the proximal and distal ends thereof.

In an embodiment, in the insertion configuration, the second anchoring element may be housed within the first lumen and, in the anchoring configuration, extends distally of the distal end of the outer member to anchor the device in a target tissue.

The present disclosure also relates to a method for treating a tissue, comprising inserting a staple device into a target tissue via a delivery catheter passed through a working channel of an endoscope, the staple device including an outer member biased to extend along a curve from a distal end to a proximal end and an inner member slidably received within a first lumen of the outer member and biased to extend along a curve from a distal end to a proximal end, the outer and inner members constrained in a straight position via an interior surface of the first lumen in an insertion configuration, the distal end of the inner member received within a proximal portion of the first lumen in the insertion configuration, moving the outer and inner members distally relative to the delivery catheter so that the outer member is inserted into a target tissue until the distal end of the outer member extends proximally of a proximal surface of the target tissue, the outer member reverting to a biased curved configuration as the outer member is moved distally out of the delivery device, and moving the device from the insertion configuration to the anchoring configuration by moving the inner member distally relative to the outer member until a first anchoring element at the proximal end of the inner member is moved distally out of the delivery catheter.

BRIEF DESCRIPTION

DETAILED DESCRIPTION

The present disclosure may be further understood with reference to the following description and the appended drawings, wherein like elements are referred to with the same reference numerals. The present disclosure is directed to devices for the treatment of tissue and, in particular endoscopic tissue treatment devices. Exemplary embodiments of the present disclosure describe an endoscopic staple including anchoring elements for anchoring the staple in a target tissue. The terms "proximal" and "distal" as used herein, refer to a direction extending toward (proximal) and away from (distal) a user of the device.

As shown in FIGS. 1-5, a staple device 100 for treating a tissue opening 10 comprises a body 101 including a base portion 102 extending along a first axis A from a first end 104 to a second end 106, a first leg 108 extending from the first end 104 along a second axis B and a second leg 110 extending from the second end 106 along a third axis C to be inserted into tissue on opposing sides of the tissue opening 10. The first and second legs 108, 110 may extend from the base portion 102 such that the second and third axes B, C are angled with respect to the base portion 102. In one embodiment, the second and third axes B, C may be perpendicular relative to the base portion 102 and parallel to one another. An angle between the first and second axes A, B and between the first and third axes A, C, however, may vary so long as the first and second legs 108, 110 extend in the same plane, along with the base portion 102, toward the same side of the base portion 102. The first and second legs 108, 110 further include first and second anchoring elements 112, 114, respectively, for anchoring the staple device 100 in the tissue into which it is inserted. The first and second anchoring elements 112, 114 are movable between an anchoring configuration, in which an engaging portion of each of the first and second anchoring elements 112, 114 extends laterally away from a corresponding one of the legs 108, 110, and an insertion configuration, in which the engaging portion of each of the anchoring elements 108, 110 is moved toward the corresponding one of the legs 108, 110.

Figure 1:
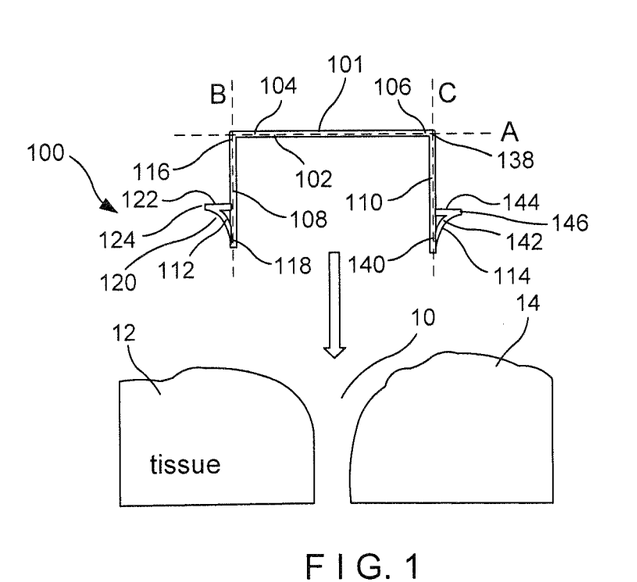
FIG. 1 shows a schematic side view of a device according to a first exemplary embodiment of the present disclosure, in a first position.

The first leg 108 extends from the first end 104 of the base portion 102 from a proximal end 116 connected to the first end 104 of the base portion 102 to a distal end 118. The first leg 108 may be hollow, including an elongated slot 134 extending through a wall thereof along a length thereof, proximally from the second end 118 so that the elongated slot 134 is open to an interior of the first leg 108. The first leg 108 includes the first anchoring element 112, which includes a first portion 120 and a second portion 122 pivotally connected to one another at a pivot point 124. The first portion 120 extends from a first end 126 connected to the distal end 118 of the first leg 108 to a second end 128. The second portion 122 extends from a first end 130 connected to the second end 128 of the first portion 120 via the pivot point 124 to a second end 132. The second end 132 of the second portion 122 includes an enlarged end 136 received within the hollow first leg 108, a cross-sectional area of the enlarged end 136 being larger than a width of the elongated slot 134 (e.g., a distance between longitudinally extending edges of the elongated slot 134) so that the enlarged end 136 is prevented from passing through the elongated slot 134 while the second portion 122 may be received therein allowing the enlarged end 136 to slide along a length of the hollow first leg 108. As the enlarged end 136 is slid along the hollow first leg 108, the first anchoring element 112 is moved between the anchoring configuration and the insertion configuration.

Figure 4:
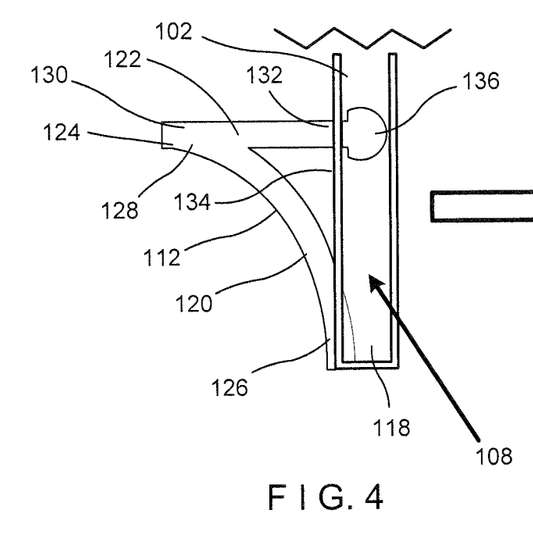
FIG. 4 shows a schematic side view of a portion of the device of FIG. 1, in an anchoring configuration.
Figure 5:
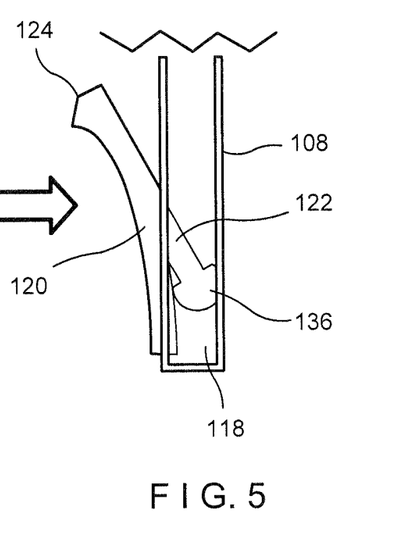
FIG. 5 shows a schematic side view of a portion of the device of FIG. 1, in an insertion configuration.

In the anchoring configuration, as shown in FIG. 4, the enlarged end 136 is received in the hollow first leg 108 proximate a proximal end of the elongated slot 134 so that the pivot point 124 extends away from the first leg 108 to engage tissue into which it is inserted. The pivot point 124 may be, for example, a living hinge biased toward the anchoring configuration. In one embodiment, the second portion 124 extends substantially perpendicular to the first leg 108 in the anchoring configuration. In the insertion configuration, as shown in FIG. 5, the enlarged end 136 is slid distally through the first leg 108 so that the enlarged end 136 is proximate a distal end of the elongated slot 134. When the enlarged end 134 is slid toward the distal end 118 of the first leg 108, the first and second portions 120, 122 are pivoted relative to one another such that the pivot point 124 is moved toward the first leg 108. Thus, in the insertion configuration, the first anchoring element 112, particularly the pivot point 124, is prevented from engaging tissue.

Figure 6:
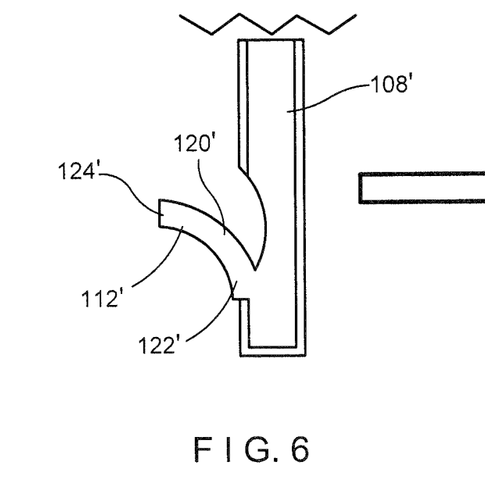
FIG. 6 shows a schematic side view of a portion of a device according to an alternate embodiment of the present disclosure, in an anchoring configuration.
Figure 7:
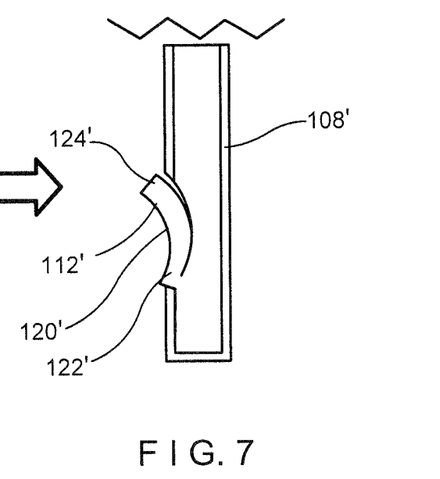
FIG. 7 shows a schematic side view of a portion of the device of FIG. 4, in an insertion configuration.

According to an alternate embodiment, as shown in FIGS. 6 and 7, a first anchoring element 112' of a first leg 108' is formed by a portion 120' of an exterior wall cut and bent away therefrom so that the portion 120' is movable between an anchoring configuration and an insertion configuration. In particular, the portion 120' extends from a distal end 122' which remains connected to the first leg 108' to a proximal end 124' which extends away from the first leg 108' in the anchoring configuration to engage a tissue into which it is inserted. The portion 120' may be, for example, heat set to be biased toward the anchoring configuration. In the insertion configuration, the proximal end 124' is moved toward the first leg 108' to facilitate insertion thereof into target tissue. Although not shown, it will be understood by those of skill in the art that an anchoring element of a second leg may be substantially similar to the anchoring element 112' of the first leg 108'.

The second leg 110 extends from a proximal end 138 connected to the second end 106 of the base portion 102 to a distal end 140 including the second anchoring element 114. The second anchoring element 114 may, for example, be substantially similar to the first anchoring element 112 of the first leg 108. In particular, the second anchoring element 114 includes first and second portions 142, 144 pivotally connected to one another at a pivot point 146 which, when in a biased anchoring configuration, extends away from the second leg 110. When in an insertion configuration, the pivot point 146 extends toward the second leg 110. Similarly to the first anchoring element 112, the second anchoring element 114 of the second leg 110 may be moved between the anchoring configuration and the insertion configuration via an enlarged end slidably received within a hollow portion of the second leg 110 via an elongated slot.

Figure 2:
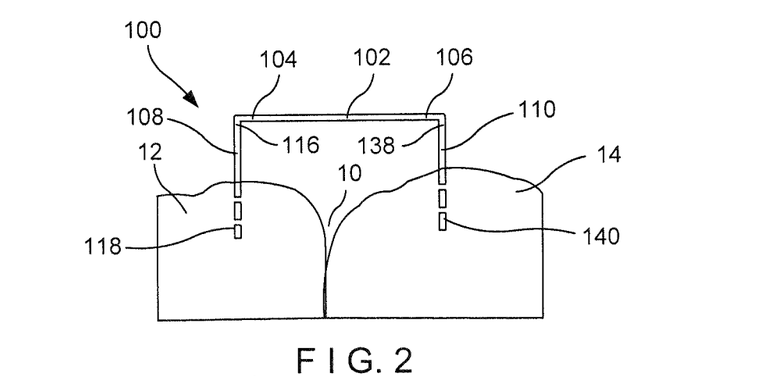
FIG. 2 shows a schematic side view of the device of FIG. 1, in a second position.
Figure 3:
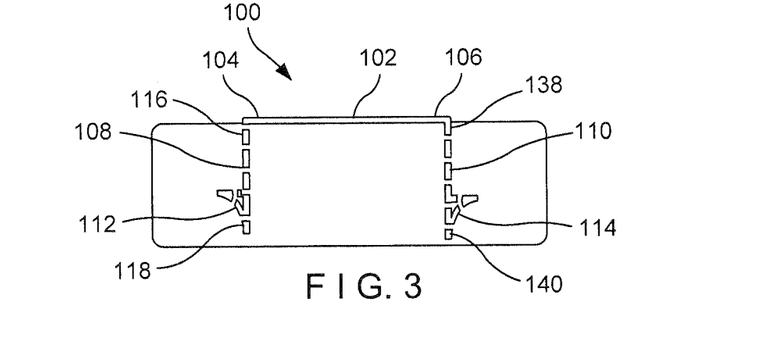
FIG. 3 shows a schematic side view of the device of FIG. 3, in a third position.

According to an exemplary surgical method using the staple device 100, the staple device 100 is inserted to a target location within a body via a working channel of an endoscope. The staple device 100 may be delivered to the target via any known stapling device. As discussed above, the first and second anchoring elements 112, 114 are biased toward the anchoring configuration so that, prior to insertion, as shown in FIG. 1, the pivot points 124, 146 thereof extend away from the first and second legs 108, 110, respectively. As the staple device 100 is inserted into the target tissue as shown in FIG. 2, however, the first portions 120, 138 of the first and second anchoring elements 112, 114, are moved toward the first and second legs 108, respectively, via a force of the tissue into which the staple device 100 is inserted. Movement of the first portions 120, 142 toward the first and second legs 108, 110 causes the pivot points 124, 146 to move toward the legs 108, 110 so that the staple device 100 is moved from the anchoring configuration to the insertion configuration. Once the staple device 100 has reached a desired position in the tissue, as shown in FIG. 3, the first and second anchoring elements 112, 114 are permitted to revert to the biased anchoring configuration. The first and second anchoring elements 112, 114 are configured to facilitate ease of insertion of the first and second legs 108, 110 distally into tissue, while preventing the staple device 100 from being moved proximally thereoutof.

In use, the first leg 108 may be inserted into a first portion of tissue 12 on a first side of the tissue opening 10 while the second leg 110 is inserted into a second portion of tissue 14 on a second side of the tissue opening 10 opposing the first side. The base portion 102 acts as a bridge connecting the first and second portions of tissue 12, 14, effectively closing the tissue opening 10. The first and second anchoring elements 112, 114 are anchored within the first and second portions of tissue 12, 14 to hold the tissue opening 10 in a closed configuration.

Figure 8:
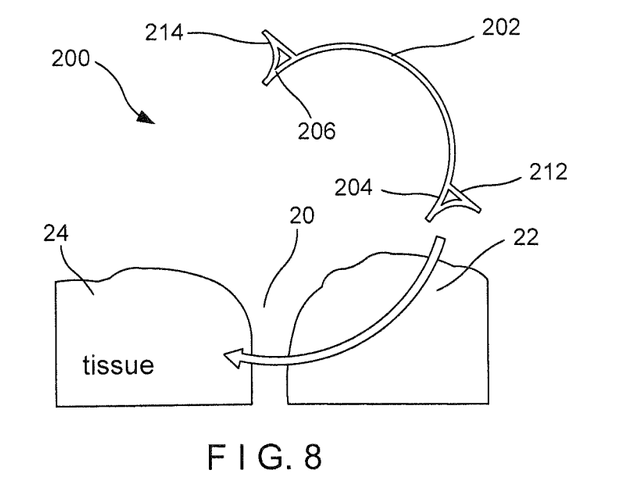
FIG. 8 shows a schematic side view of a device according to a second exemplary embodiment of the present disclosure, in a first position.
Figure 9:
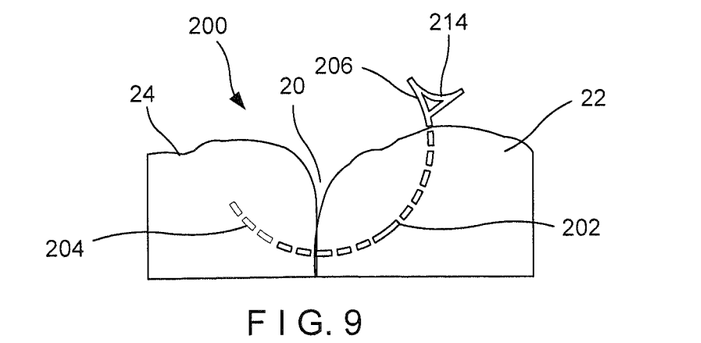
FIG. 9 shows a schematic side view of the device of FIG. 8, in a second position.
Figure 10:
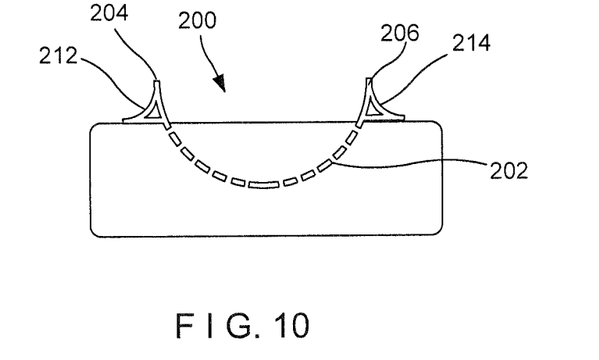
FIG. 10 shows a schematic side view of the device of FIG. 8, in a third position.

As shown in FIGS. 8-10, a staple 200 according to a second exemplary embodiment of the present disclosure is substantially similar to the staple device 100 described above. Rather than legs extending at an angle relative to a base portion, however, the staple 200 is comprised of a body 202 extending along a curve from a first end 204 to a second end 206. The first end 204 includes a first anchoring element 212 and the second end 206 includes a second element 214. The first and second anchoring elements 212, 214 are substantially similar to the first and second anchoring elements 112, 114 described above in regard to the staple device 100. The curved body 202 permits the staple device 200 to be rotated into target tissue to close a tissue opening 20. In particular, as shown in FIG. 8, the first end 204 is first inserted into a first portion 22 of tissue on a first side of the tissue opening 20 and moved across the tissue opening 20 to extend through a second portion of tissue 24 along a second side of the tissue opening 20 substantially opposing the first side. As the first end 204 is inserted into the tissue, the first anchoring element 212 is moved from a biased anchoring configuration to an insertion configuration. The first end 204 is passed through the second portion of tissue 24 until the first end 204 extends proximally of a proximal surface thereof such that the first anchoring element 212 is freed to revert to the biased anchoring configuration, as shown in FIG. 10. As shown in FIG. 10, the second anchoring element 214 prevents the second end 206 of the staple device 200 from being moved distally into the first portion of tissue 22 while the first anchoring element 212 prevents the first end 204 from being moved into the second portion of tissue 24 once it has been extended proximally therebeyond. As the staple device 200 is rotated through the first and second portions of tissue 22, 24, the staple device 200 bridges a gap between the first and second portions of tissue 22, 24, closing the tissue opening 20.

Figure 11:
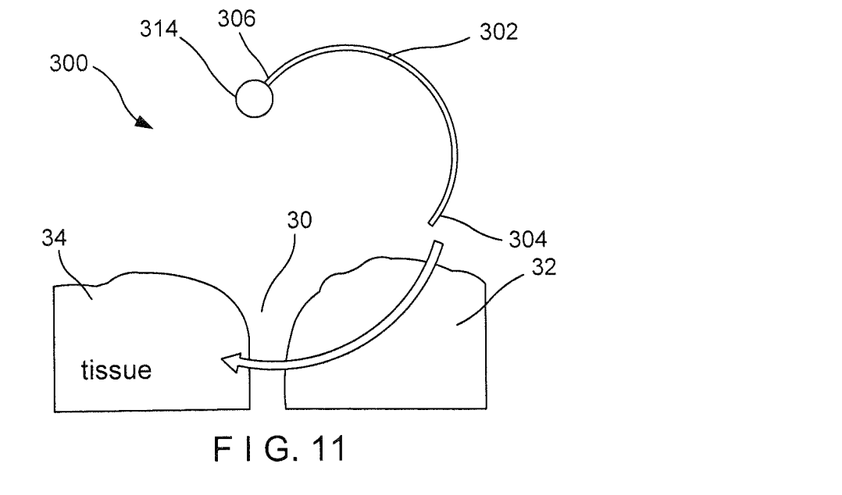
FIG. 11 shows a schematic side view of a device according to a third exemplary embodiment of the present disclosure, in a first position.
Figure 12:
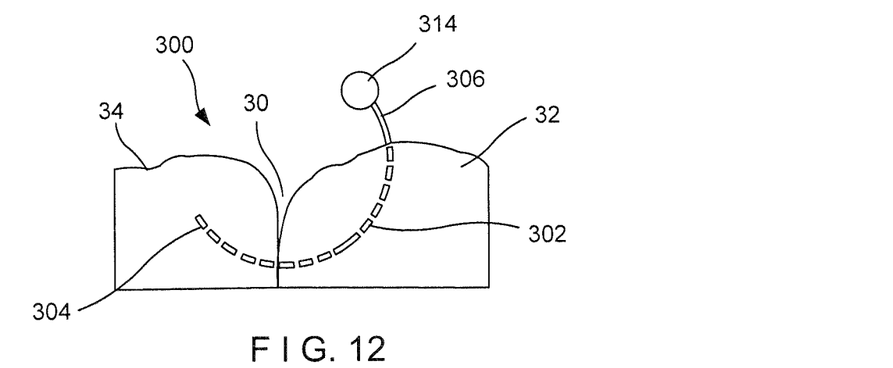
FIG. 12 shows a schematic side view of the device of FIG. 11, in a second position.
Figure 13:
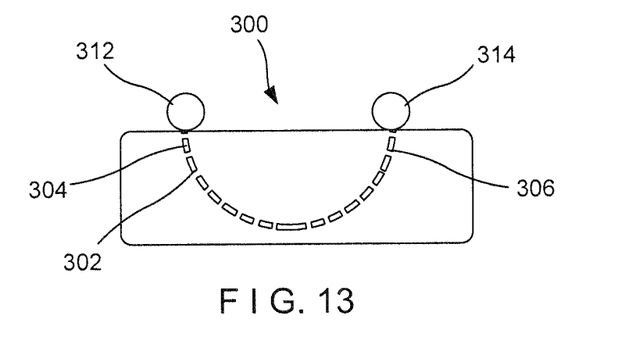
FIG. 13 shows a schematic side view of the device of FIG. 11, in a third position.

As shown in FIGS. 11-13, a staple device 300 according to a third exemplary embodiment of the present disclosure may be substantially similar to the staple device 200 comprising a curved body 302 extending from a first end 304 including a first anchoring element 312 to a second end 306 including a second anchoring element 314. The first end 304 is sharpened or tapered to facilitate piercing of a tissue into which it is inserted. The first anchoring element 312, however, may include an inflatable bulb which may be inflated via a user once the first end 304 has been inserted distally through a first portion of tissue 32 along a first side of a tissue opening 30, across the tissue opening 30 and into a second portion of tissue 34 along a second side of the tissue opening 30 substantially opposing the first side, to extend proximally from a proximal surface thereof Once the first end 304 extends proximally of the proximal surface of the first portion of tissue 32, the inflatable bulb of the first anchoring element 312 is inflated, as shown in FIG. 13. The second anchoring element 314 prevents the second end 306 of the body 302 from being moved distally through the first portion of tissue. The second anchoring element 314 may be substantially similar to the anchoring elements described above in regard to the staples 100, 200. In another embodiment, the second anchoring element 314 may also include an inflatable bulb or a cap which may be coupled to the second end 306.

According to an embodiment in which both the first and second anchoring elements are inflatable bulbs, as shown in FIGS. 14-17, the body 302 may be further comprised of an outer member 308 and an inner member 310 slidably received within the outer member 308 and movable relative to one another between an insertion configuration and an anchoring configuration. The outer member 308 is biased to extend along a curve from a first end 316 to a second 318 and includes a lumen 313 extending therethrough from the first end 316 to the second end 318. The outer member 308 includes a groove extending along an interior surface of the lumen 313. In one embodiment, the groove extends circumferentially about the interior surface of the lumen 313. The first anchoring element 312 is connected to the first end 316 of the outer member 308. The inner member 310 is also biased to extend along a curve from a first end 338 slidably received within the lumen 313 of the outer member 308 to a second end 340 and includes a lumen 315 extending therethrough. The inner member 310 also includes a stopper 311 configured as, for example, an o-ring extending about a proximal portion of the inner member 310. The stopper 311 may be configured to engage the groove extending along the interior surface of the lumen 313, when the staple device 300 is in the anchoring configuration. The second anchoring element 314 is connected to the second end 340 of the inner member 310.

The lumen 313 of the outer member 308 may be filled with a liquid for inflating the first and second anchoring elements 312, 314 upon insertion of the staple device 300 to a desired position in target tissue. In particular, when the outer and inner members 308, 310 are compressed (e.g., the inner member 310 is moved distally relative to the outer member 308) from the insertion configuration, in which the first end 338 of the inner member 310 is received within a proximal portion of the outer member 308 proximate the second end 318, toward the anchoring configuration, in which the first end 338 is moved distally toward the first end 316 of the outer member 308, the inflating liquid is displaced into the inflatable bulbs of the first and second anchoring elements 312, 314, moving the first and second anchoring elements 312, 314 from a deflated configuration to an inflated configuration to anchor the staple device 300 in the target tissue.

Figure 14:
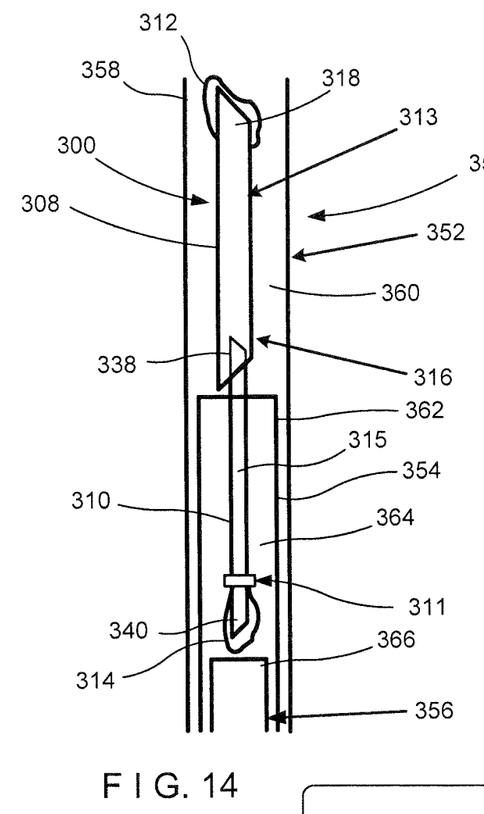
FIG. 14 shows a longitudinal cross-sectional side view of a system according to a further embodiment of the present disclosure.

The staple device 300 may be delivered to the target tissue via a delivery system 350 comprising a delivery catheter 352, a first plunger 354 and a second plunger 356. The catheter 352 extends longitudinally from a proximal end (not shown) to a distal end 358 and includes a channel 360 extending therethrough. The first plunger 354 is slidably received within the channel 360, extending from a proximal end to a distal end 362 and including a plunger channel 364 extending therethrough. The first plunger 354 is sized and shaped such that when the first plunger 354 is moved distally relative to the catheter 352, the distal end 362 abuts the second end 318 of the outer member 308 to push the outer member 308 distally out of the catheter 352. The second plunger 356 is slidably received within the plunger channel 364 of the first plunger 354, extending from a proximal end to a distal end 366. The second plunger 356 is sized and shaped such that, when the second plunger 356 is moved distally relative to the catheter 352, the distal end 366 abuts the second end 340 of the inner member 310 to push the inner member 310 distally out of the delivery catheter 352.

Figure 15:
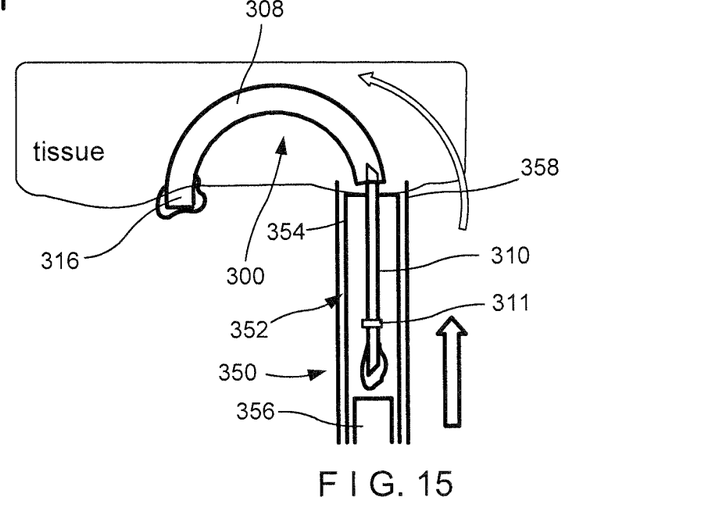
FIG. 15 shows a cross-sectional side view of the system of FIG. 14, in a first position.

The staple device 300 is loaded within the catheter 352 in the insertion configuration so that the outer member 308 is positioned distally of the first plunger 354 and the inner member 310 extends proximally from the outer member 308 and distally of the second plunger 356, as shown in FIG. 14. Although the outer and inner members 308, 310 are biased to extend along a curve, an interior surface of the channel 360 constrains the outer and inner members 308, 310 in a straightened position. The catheter 352, with the staple device 300 loaded therein, is inserted to a target location within a patient's body via, for example, a working channel of an endoscope. Once the catheter 352 has reached the target location adjacent tissue to be treated, the first and second plungers 354, 356 are moved distally relative to the catheter 352 to push the staple device 300 out of the catheter 300, in the insertion configuration, as shown in FIG. 15. The first end 316 of the outer member 308 is inserted distally into the target tissue, the outer member 308 reverting to its biased curved configuration as it extends distally out of the catheter 352. The first and second plungers 354, 356 are moved distally relative to the catheter 352 until the first end 316 of the outer member 308 curves through the target tissue to extend proximally past a proximal surface thereof.

Figure 16:
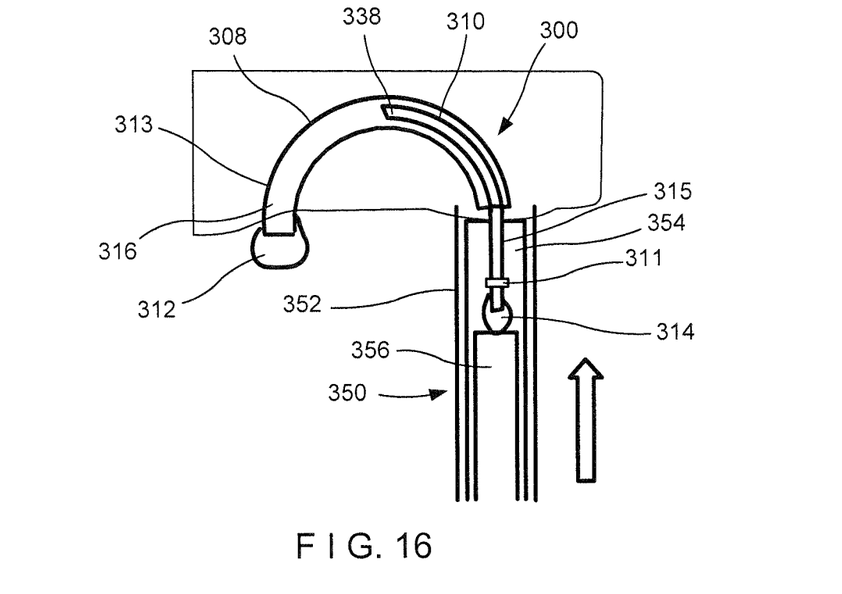
FIG. 16 shows a cross-sectional side view of the system of FIG. 14, in a second position.
Figure 17:
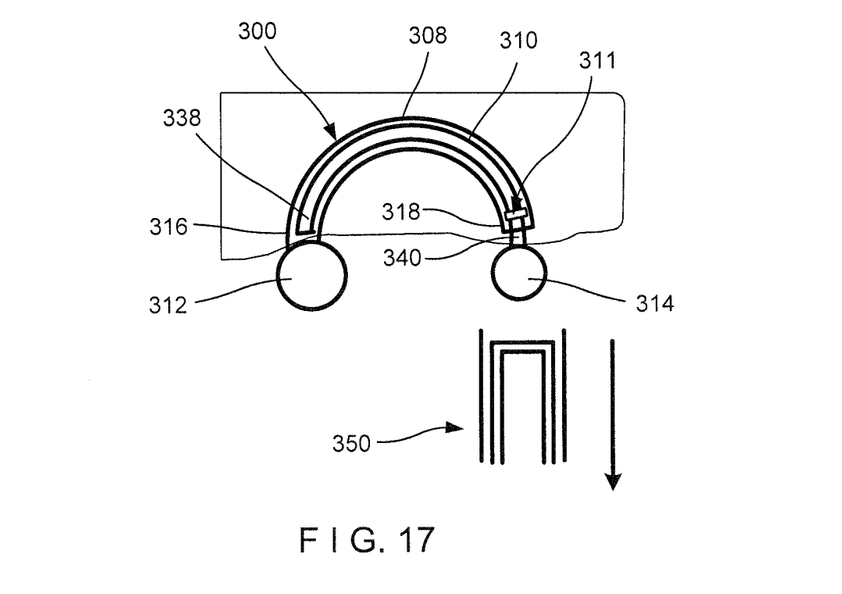
FIG. 17 shows a cross-sectional side view of the system of FIG. 15, in a third position.

Once the first end 316 is proximal of the proximal surface of the tissue, the staple device 300 is moved to the anchoring configuration by sliding the second plunger 356 distally relative to the first plunger 354, as shown in FIG. 16, to move the inner member 310 distally into the outer member 308. Compression of the outer and inner members 308, 310 causes the inflating fluid housed within the lumen 313 of the outer member 308 to become displaced, inflating the inflatable bulbs of the first and second anchoring elements 312, 314 via the lumens 313, 315, respectively, as shown in FIG. 17. The inner member 310 is moved distally relative to the outer member 308 until the stop 311 along the proximal portion of the inner member 310 engages the groove along the interior surface of the lumen 313 of the outer member 308, thereby locking the staple device 300 in the anchoring configuration in which the inflated bulbs of the first and second anchoring elements 312, 314 anchor the staple device 300 in the target tissue.

Figure 18:
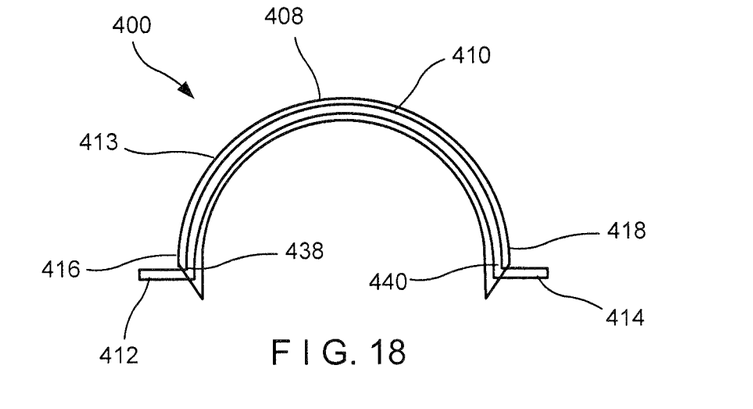
FIG. 18 shows a schematic side view of a device according to a fourth exemplary embodiment of the present disclosure.
Figure 19:
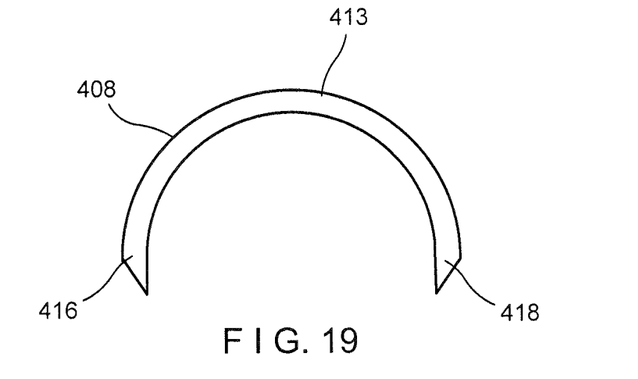
FIG. 19 shows a schematic side view of an outer member of the device of FIG. 18.
Figure 20:
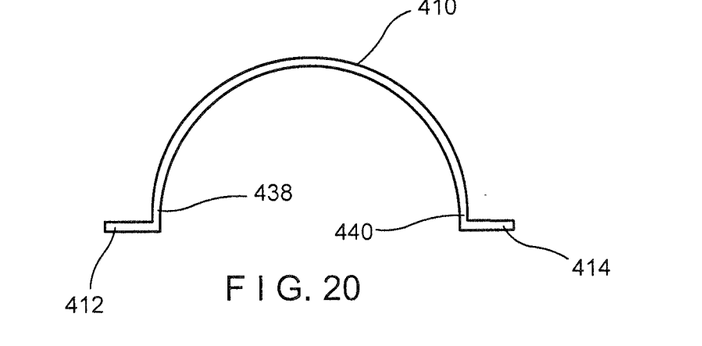
FIG. 20 shows a schematic side view of an inner member of the device of FIG. 18.

As shown in FIGS. 18-20, a staple device 400 according to a fourth exemplary embodiment of the present disclosure is substantially similar to the staple device 300 comprising an outer member 408 and an inner member 410 slidably received therein. As shown in FIG. 19, the outer member 408 is biased to extend along a curve from a first end 416 to a second end 418 and includes a lumen 413 extending therethrough. As shown in FIG. 20, the inner member 410 is also biased to extend along a curve from a first end 438 to a second end 440. The inner member 410 is slidably received within the lumen 413 of the outer member 408 and includes a first anchoring element 412 at the first end 438 and a second anchoring element 414 at the second end 440. The inner member 410 may be configured, for example, as a wire with the first and second anchoring elements 412, 414 being formed as portions of the wire bent and biased laterally away from a remaining length thereof.

The staple device 400 may be utilized in a manner substantially similar to the staple device 300. The staple device 400 is inserted to a target location in a living body using, for example, the delivery system 350 described above in regard to the staple device 300. In particular, the staple device 400 may be loaded into the delivery catheter 352 so that the outer and inner members 408, 410 are constrained in a straightened position via an interior surface of the channel 360. The staple device 400 is loaded in the catheter 352 in an insertion configuration in which the first end 438 of the inner member 410 does not extend distally from the first end 416 of the outer member 408. The staple device 400 is inserted into the target tissue in the insertion configuration, the outer member 408 reverting to its biased curved configuration as it is pushed distally out of the catheter 352 into the target tissue. Once the first end 416 of the outer member 408 extends proximally of a proximal surface of the target tissue, the inner member 410 is moved distally relative to the outer member 408 until the first end 438 of the inner member 410 extends past the first end 438 of the outer member 408 so that the first anchoring element 412 thereon reverts to its biased bent configuration. The second anchoring element 412 is also permitted to revert to its biased bent configuration as the inner member 410 is pushed entirely out of the catheter 352. Thus first and second anchoring elements 412, 414 extend out of the lumen 413 of the outer member 408, past the first and second ends 416, 418 thereof, respectively, to anchor the staple device 400 in the target tissue.

It will be apparent to those skilled in the art that various modifications may be made in the present disclosure, without departing from the scope of the disclosure. Thus, it is intended that the present disclosure cover modifications and variations of this disclosure provided that they come within the scope of the appended claims and their equivalents.

What is claimed is:

1. A device for closing a tissue opening, comprising:
a body extending from a first end to a second end; and
a first anchoring element connected to the first end of the body and a second anchoring element connected to the second end of the body, the first and second anchoring elements including a first portion and a second portion pivotally coupled to one another at a pivot point, the first portion including an enlarged end configured to be slidably received within the body, at least one of the first anchoring element and the second anchoring element movable between an insertion configuration, in which the at least one of the first and second anchoring elements is insertable through a target tissue such that the body extends across a tissue opening to be treated, and an anchoring configuration, in which the first and second anchoring elements engage target tissue on a first side and a second side, respectively, of the tissue opening.

2. The device of claim 1, wherein the body further includes a first leg extending laterally from the first end of the body with the first anchoring element extending along a portion thereof and a second leg extending laterally from the second end with the second anchoring element extending along a portion thereof.

3. The device of claim 2, wherein the first leg and the second leg extend substantially perpendicular to the body and parallel to one another.

4. The device of claim 1, wherein the first and second portions pivot pivot between the anchoring configuration, in which the pivot point extends away from a corresponding one of the first and second ends, and the insertion configuration, in which the pivot point moved toward the first and second legs.

* * * * *